United States Patent
Ito et al.

(10) Patent No.: US 12,175,564 B2
(45) Date of Patent: Dec. 24, 2024

(54) X-RAY IMAGING APPARATUS AND X-RAY IMAGE PROCESSING METHOD

(71) Applicants: LG ELECTRONICS INC., Seoul (KR); KOREA ADVANCED INSTITUTE OF SCIENCE AND TECHNOLOGY, Daejeon (KR)

(72) Inventors: Mikiko Ito, Seoul (KR); Taehyung Kim, Seoul (KR); Youngjun Jung, Seoul (KR); Byungkee Lee, Seoul (KR); Sangjun Park, Seoul (KR); Seungryong Cho, Daejeon (KR); Hyeongseok Kim, Daejeon (KR); Jeongtae Soh, Daejeon (KR)

(73) Assignees: LG ELECTRONICS INC., Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 510 days.

(21) Appl. No.: 17/443,943

(22) Filed: Jul. 28, 2021

(65) Prior Publication Data
US 2022/0405991 A1    Dec. 22, 2022

(30) Foreign Application Priority Data
Jun. 22, 2021 (KR) .................. 10-2021-0081106

(51) Int. Cl.
*G06T 11/00* (2006.01)
*A61B 6/02* (2006.01)
(Continued)

(52) U.S. Cl.
CPC ............ *G06T 11/006* (2013.01); *A61B 6/025* (2013.01); *A61B 6/4007* (2013.01);
(Continued)

(58) Field of Classification Search
CPC ..... G06T 11/003–008; G06T 2211/424; G06T 7/0012–0016; G06T 2207/10072;
(Continued)

(56) References Cited

U.S. PATENT DOCUMENTS

| | | | |
|---|---|---|---|
| 2005/0265590 A1* | 12/2005 | Li .................. | G06T 11/005 382/154 |
| 2008/0085040 A1* | 4/2008 | Basu ................ | G06T 11/005 382/128 |

(Continued)

FOREIGN PATENT DOCUMENTS

| | | |
|---|---|---|
| JP | 2798998 | 9/1998 |
| JP | 2011125698 | 6/2011 |

(Continued)

OTHER PUBLICATIONS

Park, Junyoung, et al. "Multi-beam x-ray sources with carbon nanotube emitter for tomosynthesis system." Medical Imaging 2020: Physics of Medical Imaging. vol. 11312. SPIE, 2020. (Year: 2020).*

(Continued)

*Primary Examiner* — Geoffrey E Summers
(74) *Attorney, Agent, or Firm* — LEE, HONG, DEGERMAN, KANG & WAIMEY

(57) ABSTRACT

An X-ray imaging apparatus includes an X-ray generator including a plurality of X-ray sources, an X-ray detector configured to detect X-rays radiated from the plurality of X-ray sources and generate a plurality of pieces of projection data, and a processor configured to apply log projection to each of the plurality of pieces of projection data, to apply weighted projection to the log-projected projection data, to apply a bidirectional ramp filter to the weighted-projected projection data, and to generate a tomographic image recon- (Continued)

structed based on each of the projection data to which the bidirectional ramp filter is applied.

10 Claims, 14 Drawing Sheets

(51) Int. Cl.
*A61B 6/40* (2024.01)
*G06T 7/00* (2017.01)
(52) U.S. Cl.
CPC .. *G06T 7/0012* (2013.01); *G06T 2207/10072* (2013.01); *G06T 2207/10116* (2013.01); *G06T 2211/421* (2013.01); *G06T 2211/424* (2013.01)
(58) Field of Classification Search
CPC . G06T 2207/10116; G06T 2207/10081; A61B 6/4007; A61B 6/4014; A61B 6/025; A61B 6/505; A61B 6/5205; A61B 6/02; A61B 6/5235; A61B 6/54
See application file for complete search history.

(56) References Cited

U.S. PATENT DOCUMENTS

| | | | |
|---|---|---|---|
| 2010/0215140 A1 | 8/2010 | Sauer et al. | |
| 2011/0142317 A1 | 6/2011 | Riddell | |
| 2013/0004042 A1 | 1/2013 | Yang et al. | |
| 2014/0140601 A1* | 5/2014 | Litvin | G06T 11/005 382/131 |
| 2016/0253818 A1 | 9/2016 | Tang et al. | |
| 2021/0106291 A1 | 4/2021 | Shin et al. | |
| 2022/0172425 A1* | 6/2022 | Soloviev | A61B 6/4007 |

FOREIGN PATENT DOCUMENTS

| | | |
|---|---|---|
| JP | 2016159156 | 9/2016 |
| KR | 10-1076321 | 10/2011 |
| KR | 2018-0106438 | 10/2018 |

OTHER PUBLICATIONS

Becker, Amy E., et al. "A prototype Multi-X-ray-source array (MXA) for digital breast tomosynthesis." Physics in Medicine & Biology 65.23 (2020): 235033. (Year: 2020).*
Khellaf, Feriel, et al. "2D directional ramp filter." Physics in Medicine & Biology 65.8 (2020): 08NT01. (Year: 2020).*
Lalush, David S., et al. "Tomosynthesis reconstruction from multi-beam x-ray sources." 3rd IEEE International Symposium on Biomedical Imaging: Nano to Macro, 2006.. IEEE, 2006. (Year: 2006).*
Wang, Zhenglin, et al. "Backprojection Wiener deconvolution for computed tomographic reconstruction." PloS one 13.12 (2018): e0207907. (Year: 2018).*
Wu, Gongting. Image Reconstruction and Processing for Quantitative Imaging Using Stationary Digital Tomosynthesis. Diss. University of North Carolina at Chapel Hill, 2017. (Year: 2017).*
Wells, Stephen, et al. "Modelling the use of stationary, rectangular arrays of x-ray emitters for digital breast tomosynthesis." Medical Imaging 2020: Physics of Medical Imaging. vol. 11312. SPIE, 2020. (Year: 2020).*
Korean Intellectual Property Office Application No. 10-2021-0081106, Office Action dated Jul. 19, 2022, 6 pages.
Korean Intellectual Property Office Application No. 10-2021-0081106, Notice of Allowance dated Dec. 5, 2022, 8 pages.
PCT International Application No. PCT/KR2021/008790, International Search Report dated Mar. 10, 2022, 8 pages.

* cited by examiner 1101  1102

1301  1302

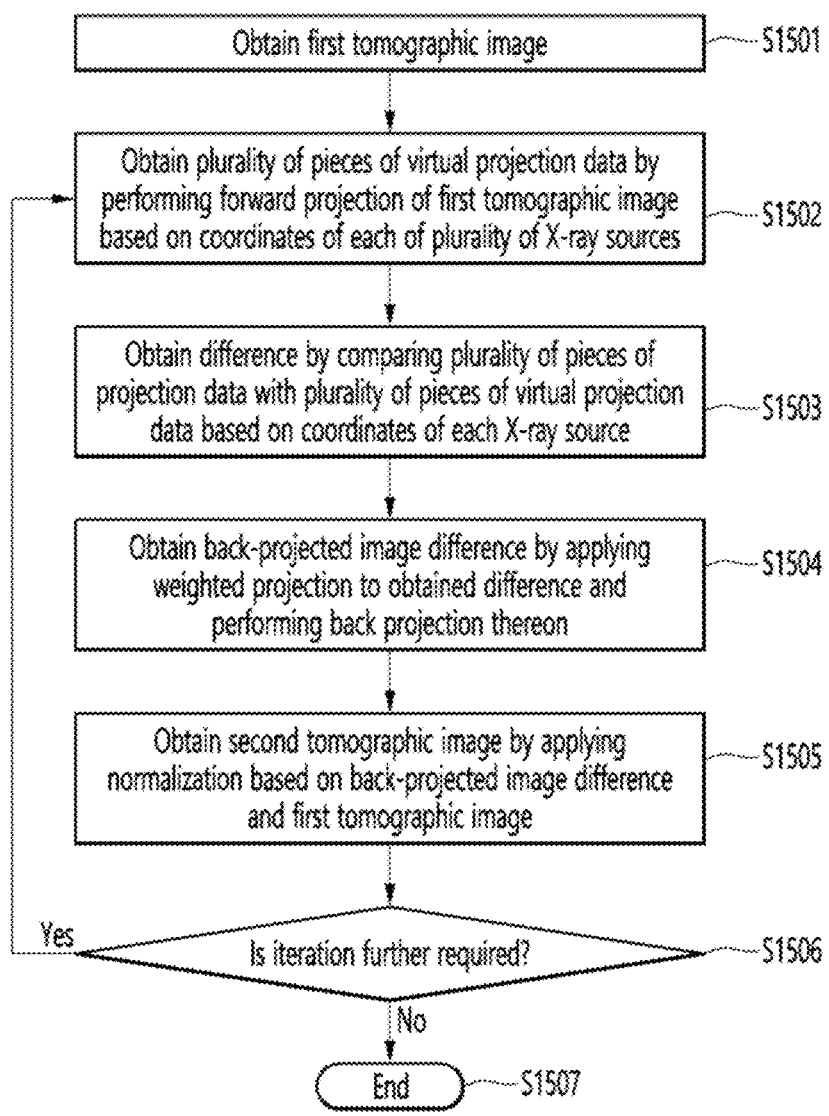

X-RAY IMAGING APPARATUS AND X-RAY IMAGE PROCESSING METHOD

CROSS-REFERENCE TO RELATED APPLICATIONS

Pursuant to 35 U.S.C. § 119(a), this application claims the benefit of earlier filing date and right of priority to Korean Patent Application No. 10-2021-0081106, filed on Jun. 22, 2021, the contents of which are hereby incorporated by reference herein in their entirety.

BACKGROUND

The present disclosure relates to an X-ray imaging apparatus and an X-ray image processing method, and more particularly, to an X-ray imaging apparatus and an X-ray image processing method for generating a tomographic image based on a plurality of pieces of projection data.

When an X-ray imaging system captures a two-dimensional (2D) X-ray image, the 2D X-ray image is an image in which X-rays are projected in one direction with respect to an object to be X-ray captured. Accordingly, as X-rays are projected onto the object in one direction, the image of the object is overlapped and covered.

On the other hand, in order to solve this problem, a representative example of an apparatus for imaging an object by radiating X-rays to a patient is computed tomography (CT) apparatus. A CT apparatus, which is a tomography apparatus among medical image processing apparatuses, may provide a cross-sectional image of an object. Compared with a general X-ray apparatus, the internal structure of the object (e.g., organs such as a kidney and a lung) may be expressed without overlapping. Therefore, the CT apparatus is widely used for precise diagnosis of disease.

However, the CT apparatus has a problem in that X-rays are captured by projecting X-rays to an object several times in various directions, which causes the radiation dose to increase.

Recently, a tomosynthesis X-ray imaging system that implements a three-dimensional (3D) image with a low dose compared to a CT apparatus has been introduced.

A tomosynthesis system is a technique that may obtain a 3D image with a low dose compared to CT, and may provide tomographic images for each depth to remove an overlapping or occlusion effect.

The tomosynthesis system generally rotates and moves an analog X-ray generator in an arc about a certain axis of rotation, and an X-ray detector also moves or rotates according to the position of the X-ray generator to capture multiple X-ray images and implement a 3D image through a reconstruction algorithm.

Therefore, since the tomosynthesis X-ray imaging system obtains images by rotating and moving using the analog X-ray generator installed together with a rail on the ceiling, there are disadvantages in that the overall size of the system increases and a larger space has to be secured for installation.

Therefore, there is a need for an X-ray imaging system capable of minimizing an occupied space and securing the convenience of installation or capable of moving.

SUMMARY

Embodiments of the present disclosure provide an X-ray imaging apparatus and an X-ray image processing method for reconstructing a 2D or 3D type tomographic image by reconstructing a plurality of pieces of projection data captured using the X-ray imaging apparatus.

Embodiments of the present disclosure provide an X-ray imaging apparatus and an X-ray image processing method capable of effectively removing discontinuous artifacts when a tomographic image is generated by reconstructing a plurality of pieces of projection data captured using an X-ray generator including a plurality of X-ray sources disposed in a one-dimensional (1D) line form or a 2D array form.

An X-ray imaging apparatus according to an embodiment of the present disclosure includes an X-ray generator including a plurality of X-ray sources, an X-ray detector configured to detect X-rays radiated from the plurality of X-ray sources and generate a plurality of pieces of projection data, and a processor configured to apply log projection to each of the plurality of pieces of projection data, to apply weighted projection to the log-projected projection data, to apply a bidirectional ramp filter to the weighted-projected projection data, and to generate a tomographic image reconstructed based on each of the projection data to which the bidirectional ramp filter is applied.

The details of one or more embodiments are set forth in the accompanying drawings and the description below. Other features will be apparent from the description and drawings, and from the claims.

BRIEF DESCRIPTION OF THE DRAWINGS

FIG. 15 is a diagram for explaining an iterative reconstruction method according to an embodiment of the present disclosure.

DETAILED DESCRIPTION OF THE EMBODIMENTS

Figure 1:
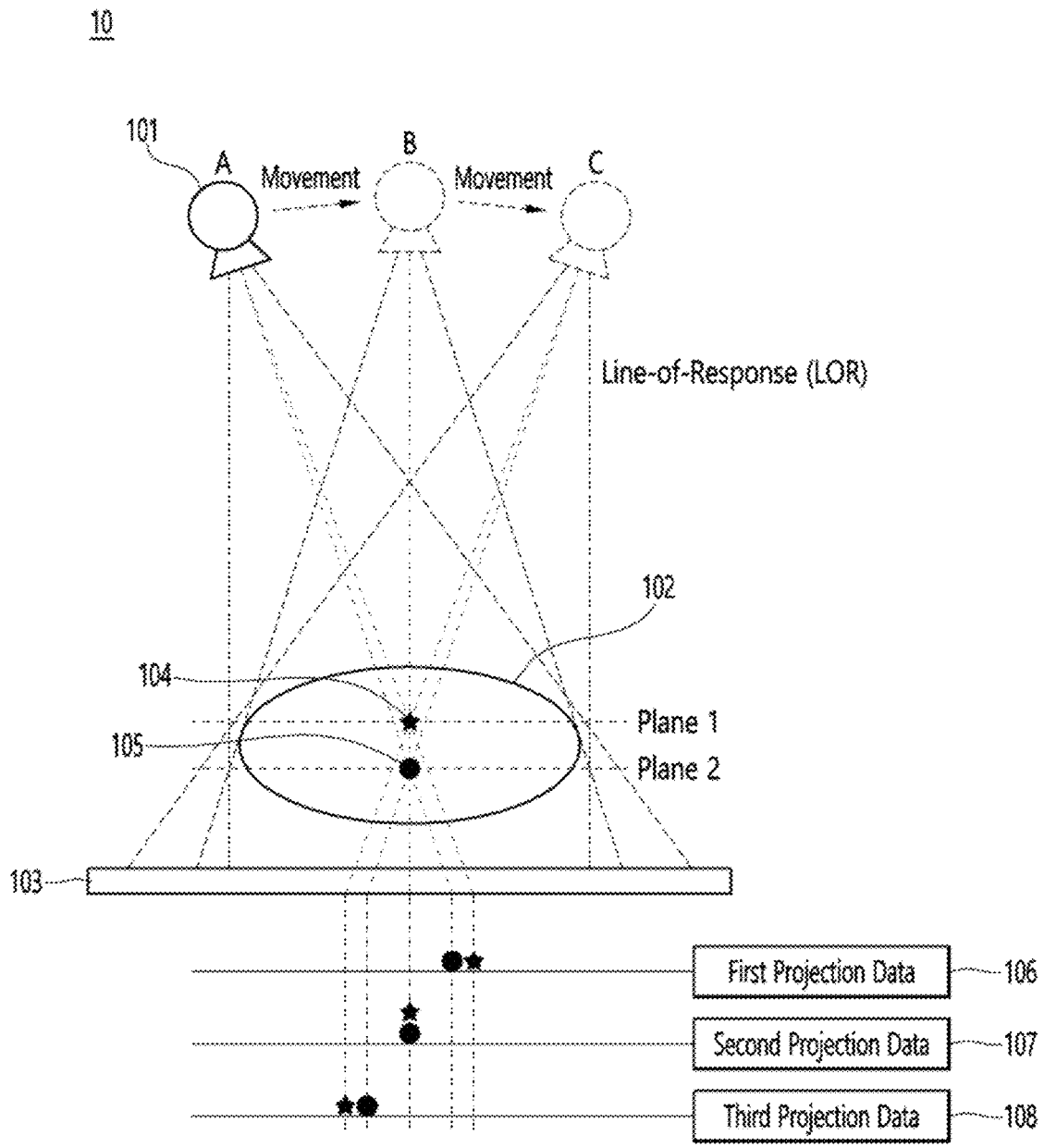
FIG. 1 is a diagram for explaining a conventional tomosynthesis system.

Hereinafter, embodiments of the present disclosure are described in more detail with reference to accompanying drawings and regardless of the drawings symbols, same or similar components are assigned with the same reference numerals and thus overlapping descriptions for those are omitted. The suffixes "module" and "unit" for components used in the description below are assigned or mixed in consideration of easiness in writing the specification and do not have distinctive meanings or roles by themselves. In the following description, detailed descriptions of well-known functions or constructions will be omitted since they would obscure the invention in unnecessary detail. Additionally, the accompanying drawings are used to help easily understanding embodiments disclosed herein but the technical idea of the present disclosure is not limited thereto. It should be understood that all of variations, equivalents or substitutes contained in the concept and technical scope of the present disclosure are also included.

It will be understood that the terms "first" and "second" are used herein to describe various components but these components should not be limited by these terms. These terms are used only to distinguish one component from other components.

In this disclosure below, when one part (or element, device, etc.) is referred to as being 'connected' to another part (or element, device, etc.), it should be understood that the former can be 'directly connected' to the latter, or 'electrically connected' to the latter via an intervening part (or element, device, etc.). It will be further understood that when one component is referred to as being 'directly connected' or 'directly linked' to another component, it means that no intervening component is present.

FIG. 1 is a diagram for explaining a conventional tomosynthesis system.

In the conventional tomosynthesis system 10, an X-ray generator 101 rotates and moves about 20 to 50 degrees with respect to a predetermined rotation axis and radiates X-rays to an object 102 to be captured. An X-ray detector 103 may generate an electrical signal corresponding to the radiation dose of transmitted X-rays.

On the other hand, when the X-ray generator 101 radiates X-rays to the object 102 to be captured while rotating and moving, the projected X-rays are detected by the X-ray detector 103 and a plurality of pieces of projection data 106, 107, 108 may be generated.

On the other hand, a first point 104 and a second point 105 may be projected by X-rays radiated by the X-ray generator 101 with respect to a first plane (Plane 1) and a second plane (Plane 2) of the object 102 to be captured, and may be mapped to the plurality of pieces of projection data 106, 107, and 108.

In this case, the first point 104 and the second point 105 mapped to the plurality of pieces of projection data 106, 107, and 108 may be differently mapped due to a change in an incident angle according to the rotational movement of the X-ray generator 101. Therefore, an operation of reconstructing a 2D or 3D X-ray tomographic image of the object 102 to be captured based on the plurality of pieces of projection data 106, 107, and 108 is additionally required.

Figure 2:
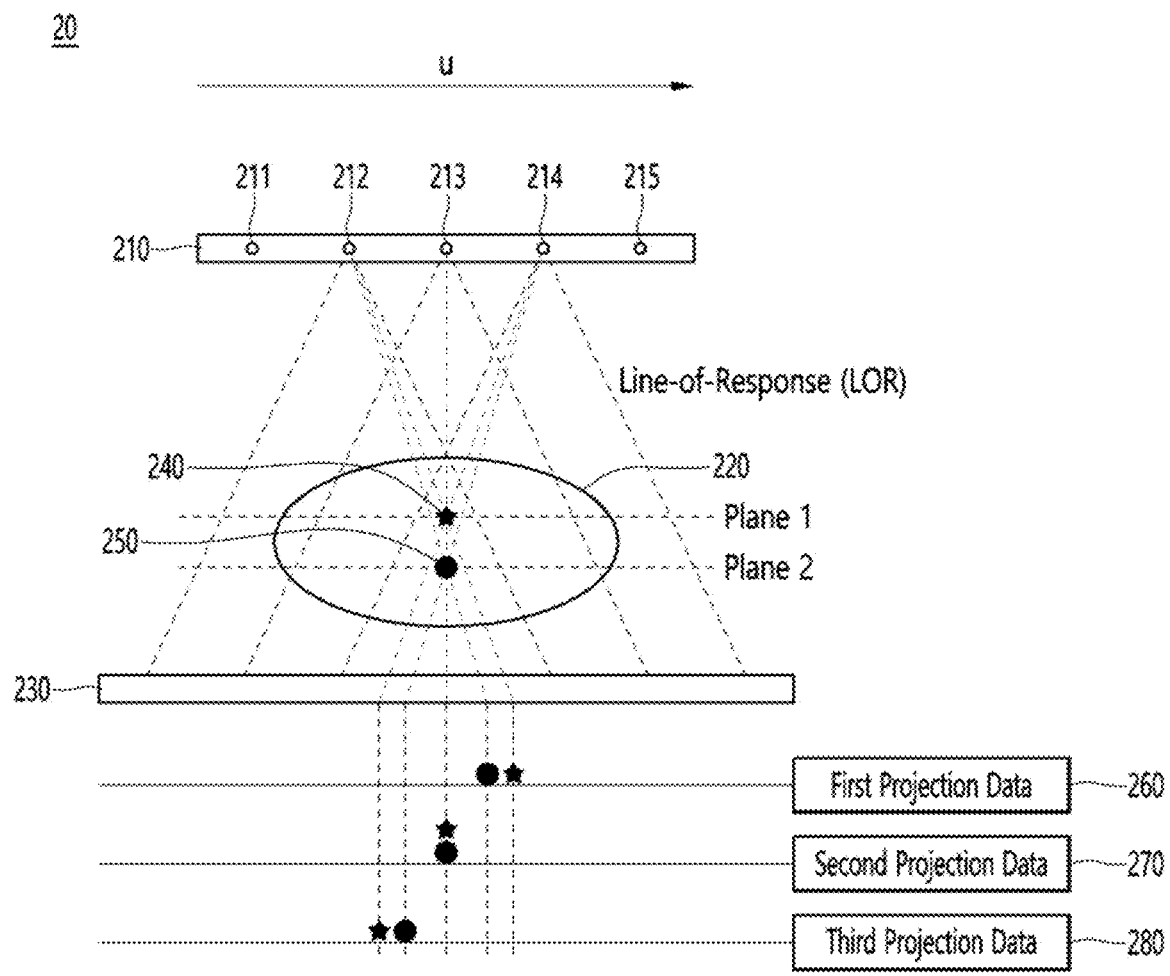
FIG. 2 is a diagram for explaining an X-ray imaging apparatus according to an embodiment of the present disclosure.

FIG. 2 is a diagram for explaining an X-ray imaging apparatus according to an embodiment of the present disclosure.

The X-ray imaging apparatus 20 includes an X-ray generator 210 in which a plurality of X-ray sources 211, 212, 213, 214, and 215 are disposed. The plurality of X-ray sources 211, 212, 213, 214, and 215 are turned on or off to radiate X-rays to the object 220 to be captured.

The X-ray detector 230 may generate an electrical signal corresponding to the radiation dose of transmitted X-rays. The X-ray sources may radiate X-rays in an electric field method.

On the other hand, the X-ray imaging apparatus 20 may have a horizontal movement method rather than the rotational movement of the conventional tomosynthesis system 10. For example, the X-ray imaging apparatus 20 may perform control so that X-rays are radiated in the order of the first X-ray source 212, the second X-ray source 213, and the third X-ray source 214.

On the other hand, a first point 240 and a second point 250 may be captured by being mapped to a plurality of pieces of projection data 260, 270, and 280 with respect to a first plane (Plane 1) and a second plane (Plane 2) of an object 102 to be captured.

In this case, the first point 240 and the second point 250 may be mapped to the plurality of pieces of projection data 260, 270, and 280 due to the horizontal movement through the on or off of the plurality of X-ray sources 211, 212, 213, 214, and 215 of the X-ray generator 210.

Therefore, an operation of reconstructing a 2D or 3D X-ray tomographic image of the object 220 to be captured based on the plurality of X-ray images 260, 270, and 280 is additionally required.

In this case, unlike the conventional tomosynthesis system 10 of FIG. 1, a tomographic image has to be generated by reflecting the characteristics of the horizontal on/off operations of the X-ray sources to reconstruct a plurality of pieces of projection data.

Figure 3:
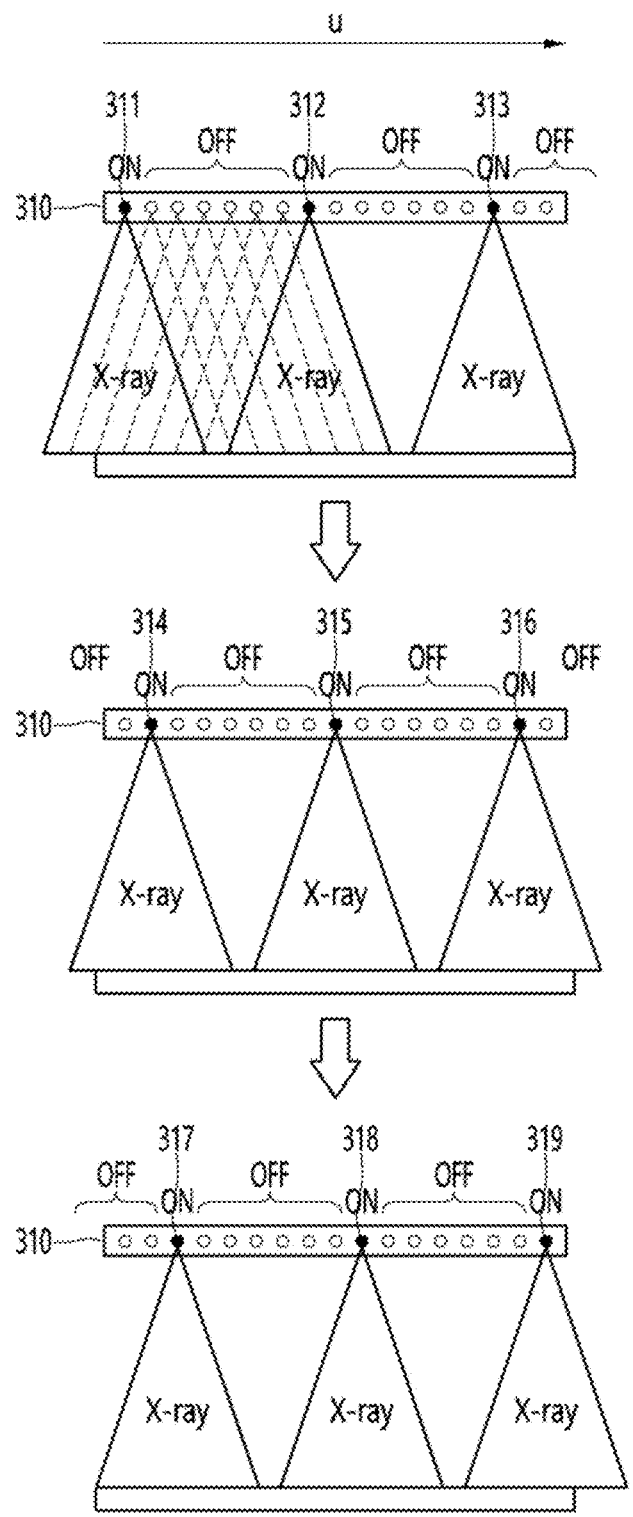
FIG. 3 is a diagram for explaining a method for capturing X-ray images through on-off control of each of a plurality of X-ray sources according to an embodiment of the present disclosure.

FIG. 3 is a diagram for explaining a method for capturing a plurality of X-ray images through on-off control of a plurality of X-ray sources according to an embodiment of the present disclosure.

The X-ray imaging apparatus 20 may control on or off of each of the plurality of X-ray sources included in the X-ray generator 210 to perform X-ray imaging on an object to be captured while horizontally moving in a first direction u.

The X-ray generator 210 operates at least one X-ray source for a predetermined time (e.g., several msec to several hundreds of msec) while maintaining the interval between the X-ray sources turned on so that the distributions of X-rays radiated on the X-ray detector 230 do not overlap. On the other hand, when the X-ray distributions overlap, the X-ray generator 210 may individually turn on or off the X-ray sources one by one.

The X-ray imaging apparatus 20 may perform control to turn on only some X-ray sources so that the X-rays radiated from the turned-on X-ray sources do not capture the object in an overlapping manner. For example, the X-ray imaging apparatus 20 may capture the object by turning on a first X-ray source 311, a second X-ray source 312, and a third X-ray source 313 among the plurality of X-ray sources included in the X-ray generator 210.

Thereafter, the X-ray imaging apparatus 20 may capture the object by turning on a fourth X-ray source 314, a fifth X-ray source 315, and a sixth X-ray source 316. In addition, the X-ray imaging apparatus 20 may capture the object by sequentially turning on a seventh X-ray source 317, an eighth X-ray source 318, and a ninth X-ray source 319.

On the other hand, the X-ray imaging apparatus 20 may simultaneously transmit a predetermined signal to the X-ray detector 230 when one or more X-ray sources are turned on, and may obtain and store projection data whenever each X-ray source is turned on.

Figure 4:
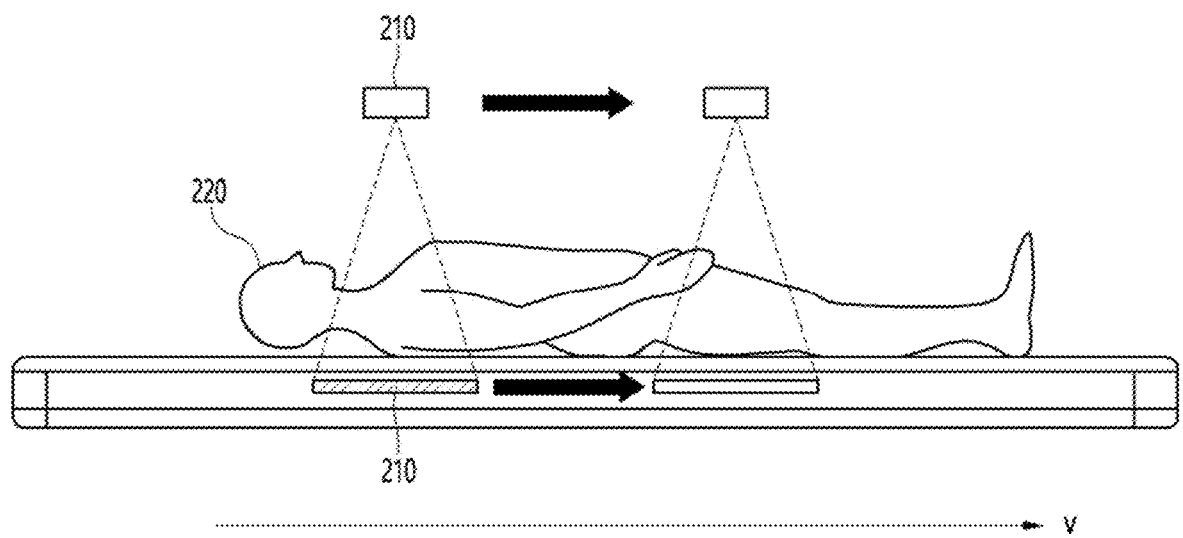
FIGS. 4 and 5 are diagrams for explaining a method of capturing an X-ray image through an X-ray imaging apparatus according to an embodiment of the present disclosure.
Figure 5:
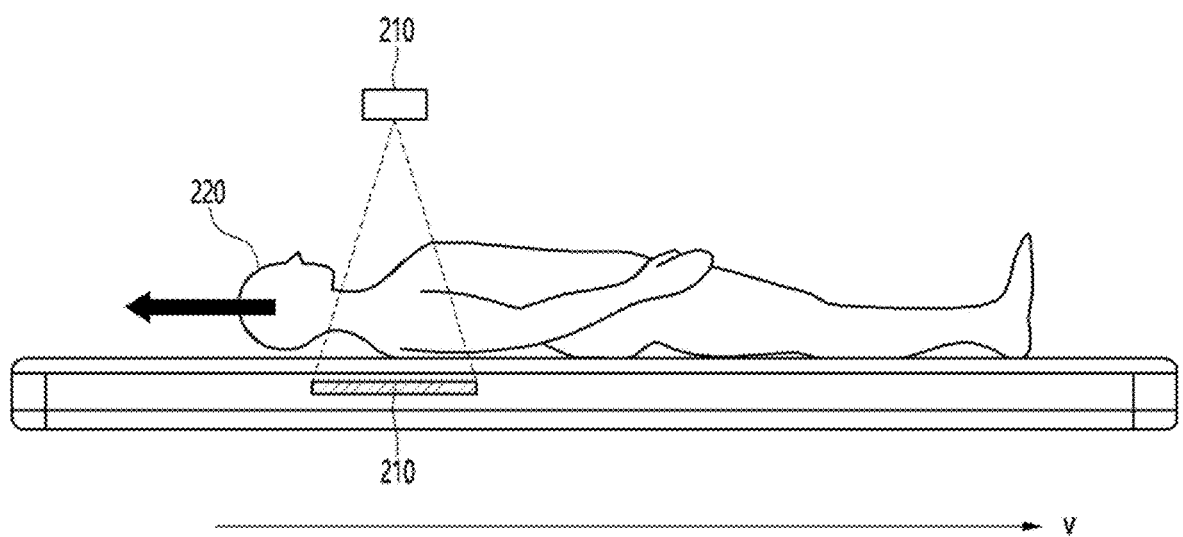

FIGS. 4 and 5 are diagrams for explaining a method of capturing an X-ray image through an X-ray imaging apparatus according to an embodiment of the present disclosure.

Referring to FIG. 4, in the X-ray imaging apparatus 20 according to an embodiment of the present disclosure, an X-ray generator 210 or an X-ray detector 230 may capture an X-ray image of an object 220 while horizontally moving in a second direction v.

Alternatively, referring to FIG. 5, in the X-ray imaging apparatus 20 according to an embodiment of the present disclosure, an X-ray image may be captured while the X-ray generator 210 or the X-ray detector 230 is fixed and the object 220 to be captured horizontally moves in the second direction v.

Figure 6:
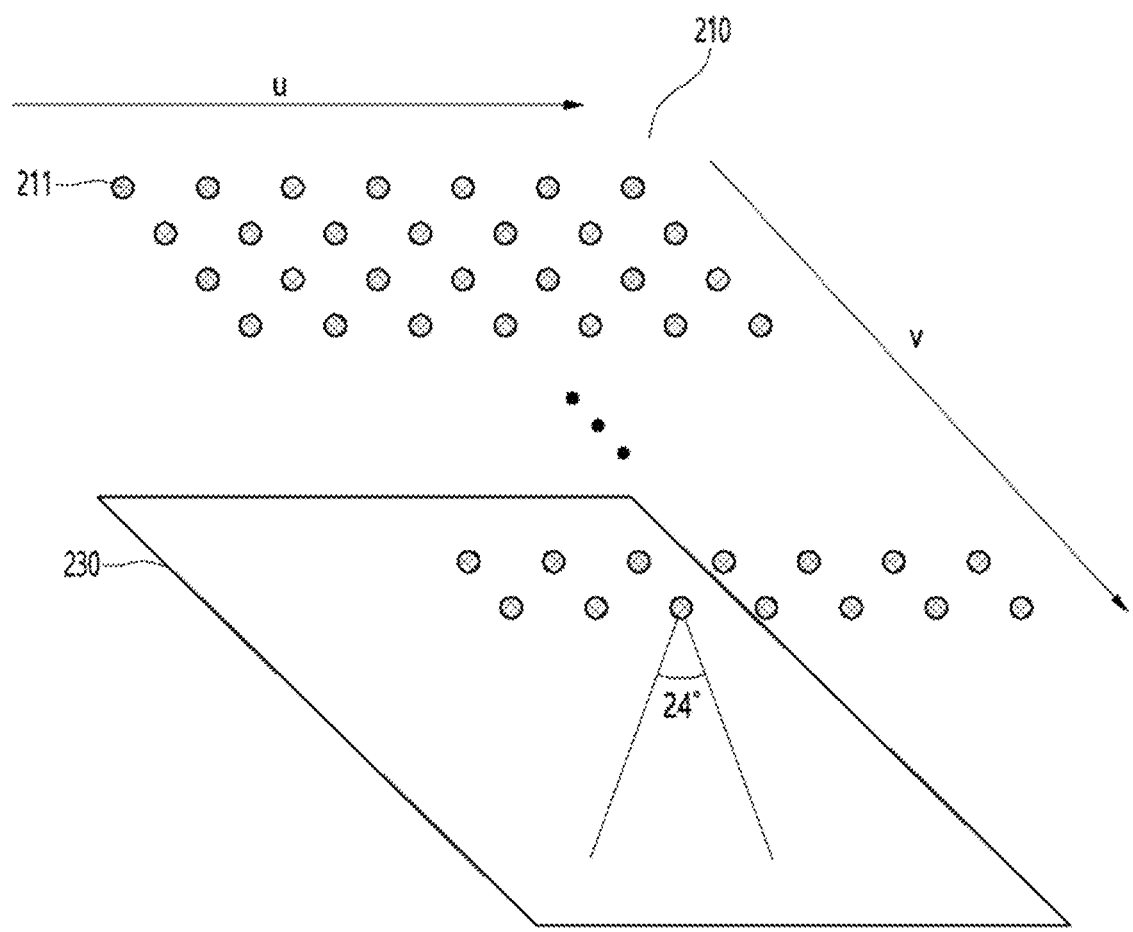
FIG. 6 is a diagram for explaining an X-ray generator in which a plurality of X-ray sources are disposed in a two-dimensional (2D) array according to an embodiment of the present disclosure.

FIG. 6 is a diagram for explaining an X-ray generator in which a plurality of X-ray sources are disposed in a 2D array according to an embodiment of the present disclosure.

The plurality of X-ray sources 211 of the X-ray generator 210 may be arranged in a 2D array. The X-ray imaging apparatus 20 may capture an X-ray image by controlling each of the plurality of X-ray sources 211 to be turned on or off in the first direction u or the second direction v. Therefore, an object may be captured with the same effect as the case in which an X-ray generator in which a plurality of X-ray sources are disposed in a 1D line shape moves horizontally.

Figure 7:
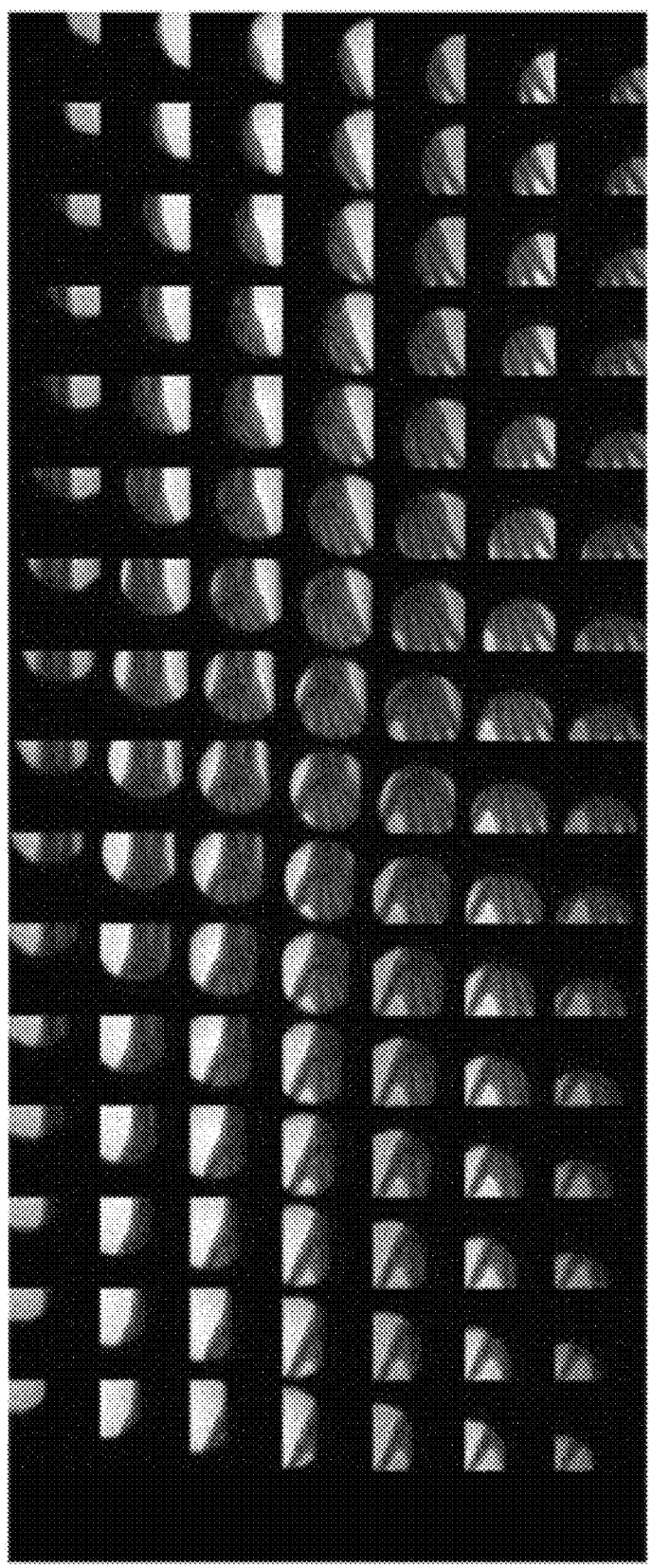
FIG. 7 is a diagram illustrating a plurality of pieces of projection data obtained by an X-ray imaging apparatus according to an embodiment of the present disclosure.

On the other hand, FIG. 7 is a diagram illustrating a plurality of pieces of projection data obtained by the X-ray imaging apparatus according to an embodiment of the present disclosure.

A plurality of pieces of projection data 700 may be an X-ray projection image projected when X-rays radiated while the plurality of X-ray sources of the X-ray generator 210 are sequentially turned on or off in the first direction u or the X-ray generator 210 moves horizontally in the second direction v are detected by the X-ray detector 230.

The X-ray imaging apparatus 20 may reconstruct a 2D or 3D X-ray image that is the tomographic image of the object to be captured based on the plurality of pieces of projection data 700.

Figure 8:
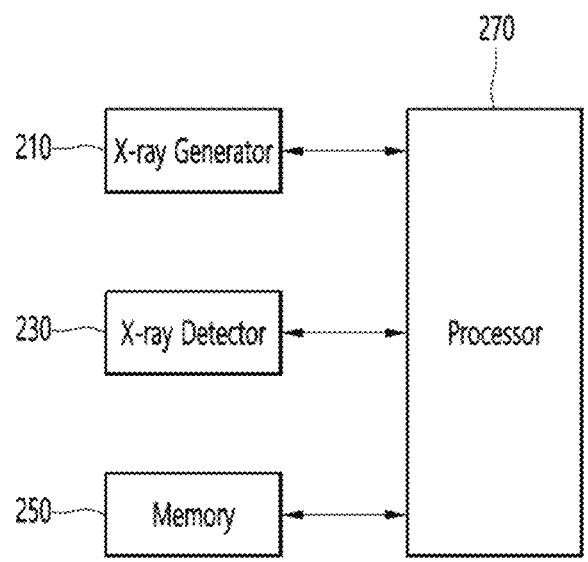
FIG. 8 is a block diagram illustrating an X-ray imaging apparatus according to an embodiment of the present disclosure.

On the other hand, FIG. 8 is a block diagram illustrating an X-ray imaging apparatus according to an embodiment of the present disclosure.

The X-ray imaging apparatus 20 may include an X-ray generator 210, an X-ray detector 220, a memory 250, and a processor 270.

The X-ray generator 210 may include a plurality of X-ray sources. The plurality of X-ray sources may be arranged in a 1D line form or in a 2D array form.

The X-ray detector 230 may generate an electrical signal corresponding to the radiation dose of transmitted X-rays. The X-ray detector 230 may generate an electrical signal to generate projection data.

The memory 250 may store a program for processing and controlling each signal in the processor 270, and may store a signal-processed image, audio, or data signals. The memory 250 may store a plurality of pieces of projection data.

The processor 270 may control the movement of the X-ray generator 210 or the X-ray detector 230, or may control on or off of each of the plurality of X-ray sources of the X-ray generator 210.

In addition, the processor 270 may store the plurality of pieces of projection data generated by the X-ray detector 230 in the memory 250.

In addition, the processor 270 may reconstruct the plurality of pieces of projection data into a 2D or 3D X-ray image that is a tomographic image of an object to be captured. For example, the processor 270 may generate the 2D or 3D X-ray tomographic image by applying a predetermined reconstruction algorithm based on the plurality of pieces of projection data.

On the other hand, a representative example of the reconstruction algorithm is a filtered back projection (FBP) reconfiguration algorithm. However, when the FBP reconstruction algorithm used in the conventional tomosynthesis system 10 disclosed in FIG. 1 is used in the X-ray imaging apparatus 20 of FIG. 2, artifacts may occur in the reconstructed X-ray image. In the conventional tomosynthesis system 10, the X-ray generator rotates about a predetermined axis of rotation to obtain projection data, but the X-ray imaging apparatus 20 of FIG. 2 horizontally moves to obtain projection data. Thus, since X-rays are incident on a portion of the X-ray detector at a limited angle, only a portion of projection data is used to calculate one pixel value. Therefore, discontinuous linear image artifacts may appear in the reconstructed X-ray image.

Figure 9:
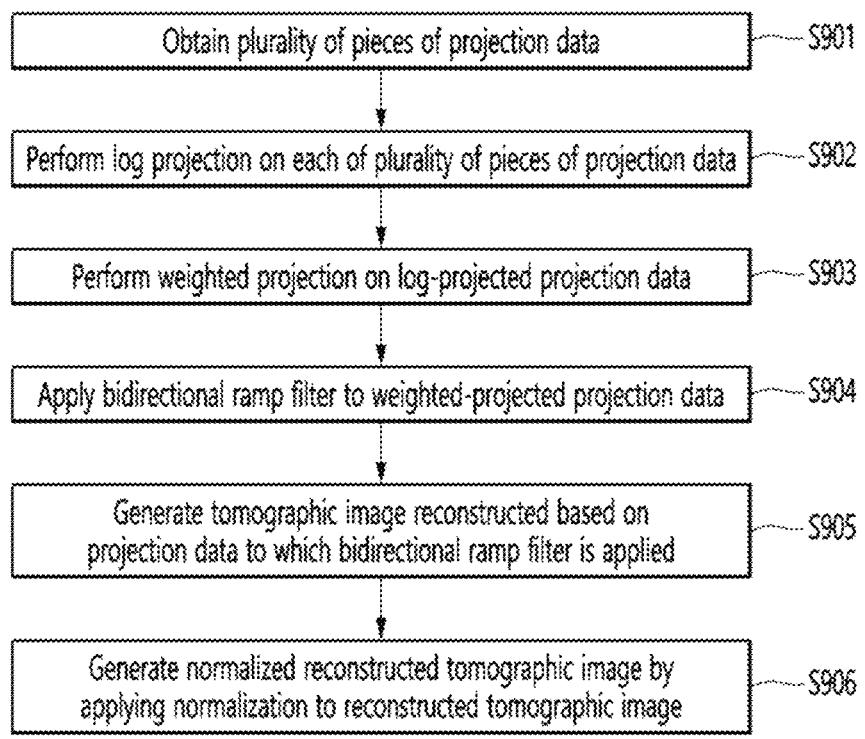
FIG. 9 is a flowchart illustrating an X-ray image processing method according to an embodiment of the present disclosure.

FIG. 9 is a flowchart illustrating an X-ray image processing method according to an embodiment of the present disclosure.

The processor 270 may obtain a plurality of pieces of projection data (S901). For example, the processor 270 may obtain a plurality of pieces of projection data generated by the X-ray detector 230 and stored in the memory 250.

The processor 270 may generate log-projected projection data by performing log projection on each of the plurality of pieces of projection data (S902). The log projection may be to change the exponential characteristics of the projection data reflected due to the exponential absorption of X-rays by the object 220 to a log scale so that the projection data has a linear value.

In addition, the processor 270 may generate weighted-projected projection data by performing weighted projection on the log-projected projection data (S903).

Referring to the plurality of pieces of projection data 700 of FIG. 7, each projection data has a boundary of an X-ray radiation area for a portion of the object to be captured. Accordingly, artifacts may occur near the boundary line when back-projected onto a field of view (FOV) area corresponding to the projection data. Therefore, the processor 270 may generate weighted-projected projection data by performing weighted projection on the log-projected projection data, thereby reducing artifacts occurring near the boundary line.

Figure 10:
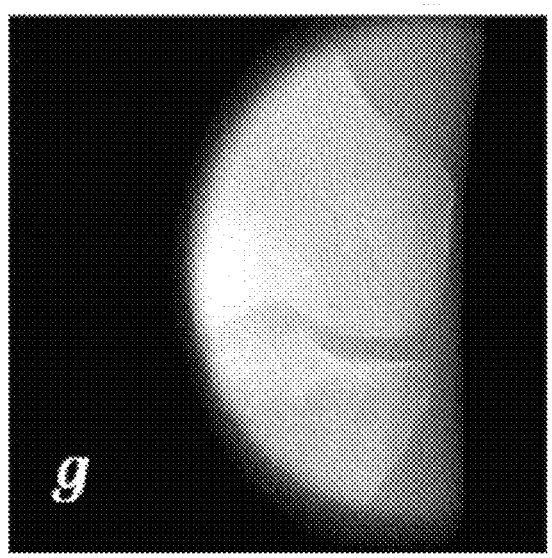
FIG. 10 is a diagram for explaining a weighted projection method according to an embodiment of the present disclosure.
Figure 10:
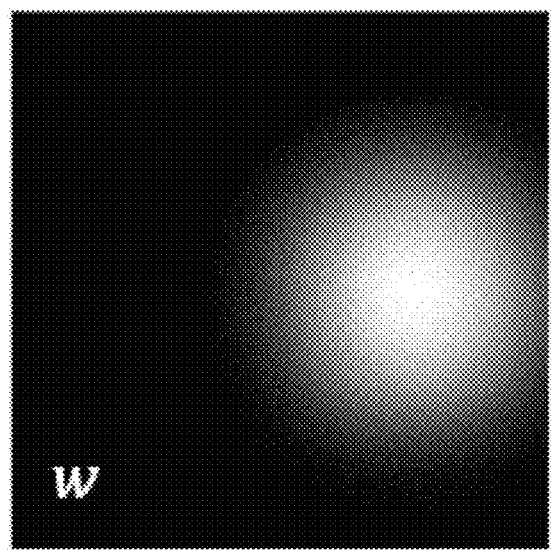
Figure 10:
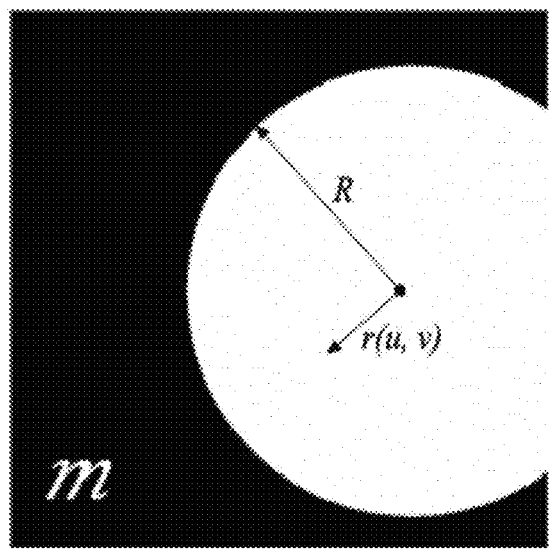

FIG. 10 is a diagram for explaining a weighted projection method according to an embodiment of the present disclosure.

The processor 270 may generate weighted-projected projection data ($g_w$) by applying a weight (w) to log-projected projection data (g). Equation 1 below may be applied to the weighted projection.

$$g_w = g \cdot w$$

$$w(u,v) = \cos^2(\pi r(u,v)/(2*R)) \quad \text{[Equation 1]}$$

u and v may be coordinates of the X-ray source.

Figure 11:
FIG. 11 is a diagram for comparing a tomographic image to which weighted projection is applied according to an embodiment of the present disclosure with a tomographic image reconstructed using a conventional technique.
Figure 11:

FIG. 11 is a diagram for comparing a tomographic image to which weighted projection is applied according to an embodiment of the present disclosure with a tomographic image reconstructed using a conventional technique.

When a tomographic image 1101 reconstructed using the conventional technique is compared with a tomographic image 1102 to which weighted projection is applied, it can be seen that artifacts occurring near the boundary line are reduced.

On the other hand, the processor 270 may apply a bidirectional ramp filter to weighted-projected projection data $g_w$, to generate projection data to which a bidirectional ramp filter is applied (S904).

Figure 12:
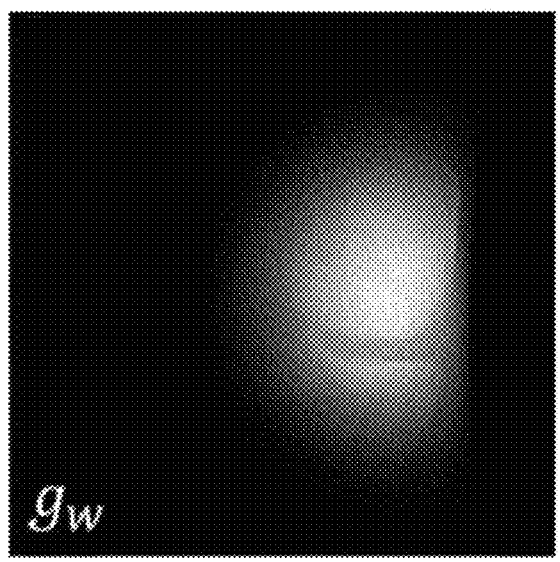
FIG. 12 is a diagram for explaining a method for applying a bidirectional ramp filter according to an embodiment of the present disclosure.
Figure 12:
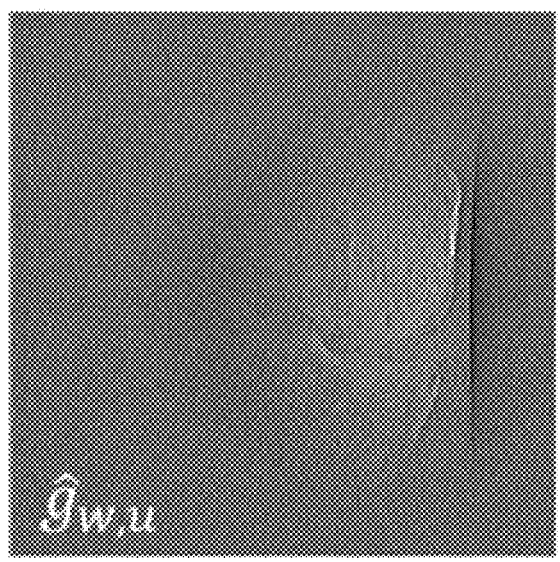
Figure 12:
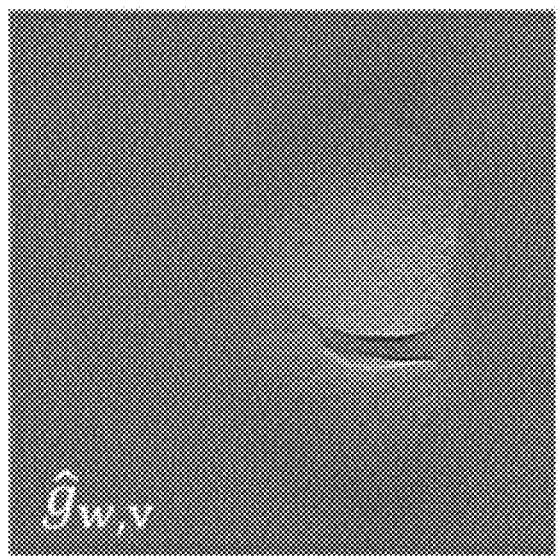
Figure 12:
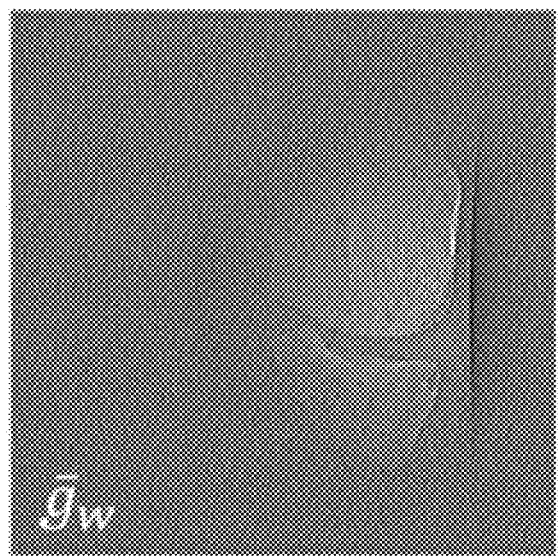

FIG. 12 is a diagram for explaining a method for applying a bidirectional ramp filter according to an embodiment of the present disclosure.

The ramp filter may be a filter for emphasizing a high frequency component in a predetermined direction in order to compensate for asymmetric appearance of a frequency component according to a direction of obtaining the projection data. Therefore, an effect of appearing an object more clearly may be exhibited.

The X-ray imaging apparatus 20 according to an embodiment of the present disclosure sequentially radiates X-rays to the object to be captured in each of the first direction (e.g., u direction) and the second direction (e.g., v direction) to obtain projection data. Since the image is captured by horizontal movement in the first direction u or the second direction v, an area in which the object to be captured disappears is generated in each of the plurality of pieces of projection data.

For example, when the X-ray generator 210 includes a plurality of X-ray sources disposed in a 1D line form, the plurality of X-ray sources are sequentially turned on and radiate X-rays to the object to be captured in the first direction. In addition, the X-ray generator 210 may move in the second direction to capture an image.

Accordingly, when a 1D ramp filter is applied in only one direction to each of a plurality of pieces of projection data, objects in the projection data may be blurred in only one direction, resulting in an asymmetric shape.

Therefore, the processor 270 may apply the ramp filter in both directions (the first direction and the second direction).

Referring to FIG. 12, the processor 270 may obtain projection data ($\hat{g}_{w,u}$) to which the ramp filter is applied to weighted-projected projection data ($g_w$) in the first direction u. In addition, the processor 270 may obtain projection data ($\hat{g}_{w,v}$) to which the ramp filter is applied to weighted-projected projection data ($g_w$) in the second direction v. In addition, the processor 270 may obtain projection data ($\bar{g}_w$) to which the ramp filter is applied to weighted-projected projection data ($g_w$) in both directions. The following equation may be applied to the projection data ($\bar{g}_w$) to which the ramp filter is applied in both directions.

$$\bar{g}_w = w_u \hat{g}_{w,u} + (1-w_u) \hat{g}_{w,v} \quad \text{[Equation 2]}$$

Figure 13:
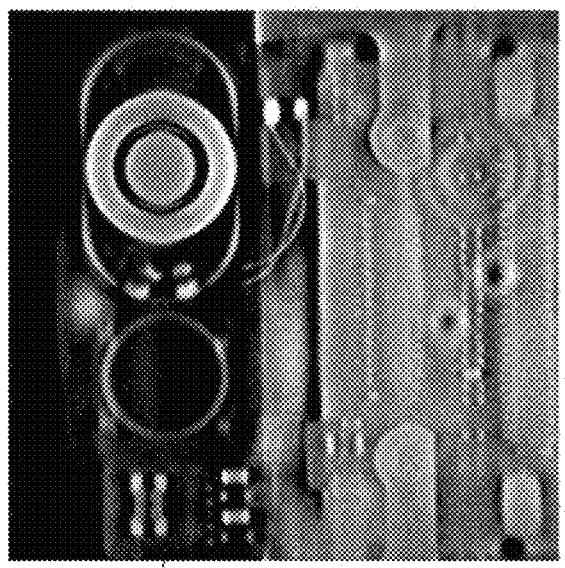
FIG. 13 is a diagram for comparing a tomographic image to which a bidirectional ramp filter is applied according to an embodiment of the present disclosure with a tomographic image reconstructed using a conventional technique.
Figure 13:
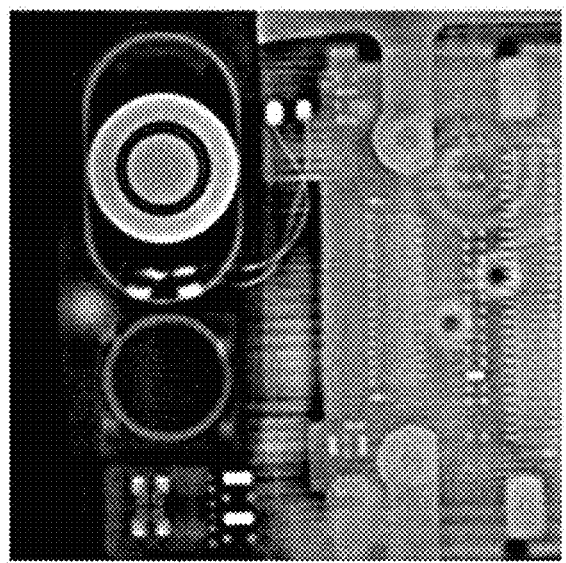

FIG. 13 is a diagram for comparing a tomographic image to which a bidirectional ramp filter is applied according to an embodiment of the present disclosure with a tomographic image reconstructed using a conventional technique.

When the tomographic image 1301 reconstructed using the conventional technique is compared with the tomographic image 1302 to which the bidirectional ramp filter is applied, it can be seen that the phenomenon in which objects are blurred in only one direction and thus an asymmetric shape occurs is reduced.

On the other hand, the processor 270 may generate a reconstructed tomographic image based on each of the projection data to which the bidirectional ramp filter is applied (S905). In this case, a reconstruction image step in a general FBP algorithm may be applied.

In addition, the processor 270 may generate a normalized reconstructed tomographic image by applying normalization to the reconstructed tomographic image (S906).

Figure 14:
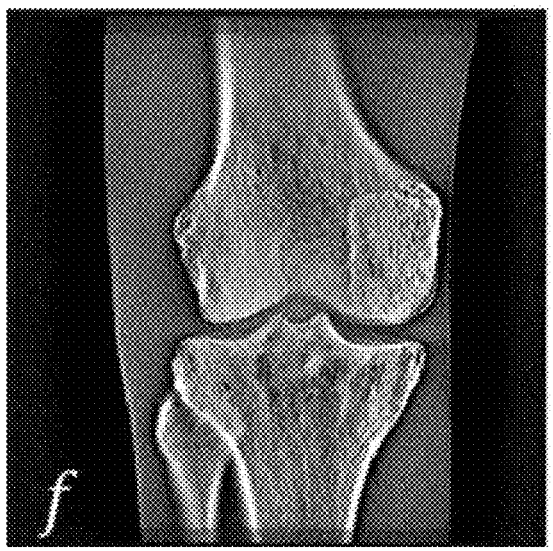
FIG. 14 is a diagram for explaining a method for generating a normalized tomographic image according to an embodiment of the present disclosure.
Figure 14:
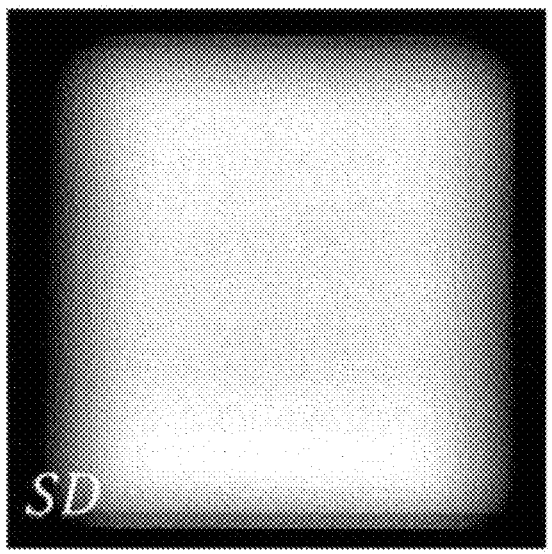
Figure 14:
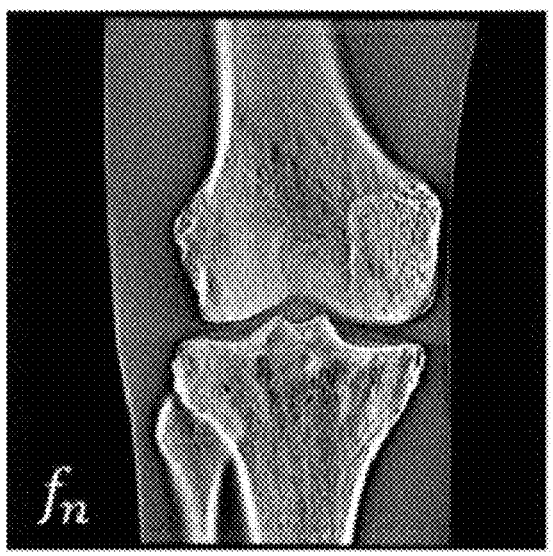

FIG. 14 is a diagram for explaining a method for generating a normalized tomographic image according to an embodiment of the present disclosure.

The plurality of pieces of projection data are data captured by horizontal movement of a plurality of X-ray sources in a first direction or a second direction. Accordingly, more X-rays may be radiated from the edge of the object to the center of the object to be captured, and more pixels overlap the projection data toward the center of the object to be captured.

Accordingly, the processor 270 may generate a sampling density (SD) map by reconstructing weights used in weighted projection, and divide the reconstructed tomographic image ($f$) to generate a normalized reconstructed tomographic image ($f_n$). The following equation may be applied to the reconstructed tomographic image ($f$), the SD map, and the normalized reconstructed tomographic image ($f_n$).

$$f(\vec{x}) = \sum_{i=1}^{N} \bar{g}_{w,i}(\vec{u}(i, \vec{x})) \quad \text{[Equation 3]}$$

$$SD = \sum_{i=1}^{N} w(\vec{u}(i, \vec{x}))$$

$N$: total number of sources $f_n = f/SD$

FIG. 15 is a diagram for explaining an iterative reconstruction method according to an embodiment of the present disclosure.

On the other hand, the processor 270 may iteratively perform the reconstruction process again after initially obtaining the normalized reconstructed tomographic image. In this case, the processor 270 may use a Maximum Likelihood-Expectation Maximization (ML-EM) algorithm or the like.

The processor 270 may repeat the iterative reconstruction process with respect to the normalized reconstructed tomographic image until an iteration criterion is satisfied. The iteration criterion may be set to a predetermined number of iterations.

The processor 270 may obtain the initially generated normalized reconstructed tomographic image as a first tomographic image (S1501).

The processor 270 may obtain a plurality of pieces of virtual projection data by performing forward projection of the first tomographic image based on the coordinates (u, v) of each of the plurality of X-ray sources (S1502).

The processor 270 may obtain a difference or a ratio by comparing the plurality of pieces of projection data obtained by radiating X-rays to the object to be captured with the plurality of pieces of virtual projection data, based on the coordinates of each X-ray source (S1503).

The processor 270 may obtain a back-projected image difference or ratio (back-project ratio) by applying weighted projection to the obtained difference or ratio (S1504).

In addition, the processor 270 may obtain a second tomographic image by applying normalization based on the back-projected image difference or ratio and the first tomographic image (S1505).

In addition, the processor 270 may determine whether iteration is further required (S1506). For example, when a predetermined number of iterations is satisfied, the processor 270 may determine that further iterations are not necessary and may end the iterative reconstruction (S1507). In addition, for example, when the predetermined number of iterations is not satisfied, the processor 270 may determine that iterations are further necessary and may perform a reconstruction process again on the second tomographic image (S1502).

On the other hand, an (n+1)-th tomographic image that has undergone the iterative reconstruction process for an n-th tomographic image may satisfy the following equation.

$$f_j^{(n+1)} = \frac{f_j^{(n)}}{\sum_i h_{ij}} \sum_i h_{ij} \frac{g_i}{\sum_k h_{ik} \hat{f}_k^{(n)}}$$ [Equation 4]

According to embodiments of the present disclosure, it is possible to provide an X-ray imaging apparatus capable of effectively removing discontinuous artifacts when a tomographic image is generated by reconstructing a plurality of pieces of projection data captured using an X-ray generator including a plurality of X-ray sources disposed in a 1D line form or a 2D array form.

The above description is merely illustrative of the technical idea of the present disclosure, and various modifications and changes may be made thereto by those skilled in the art without departing from the essential characteristics of the present disclosure.

Therefore, the embodiments of the present disclosure are not intended to limit the technical spirit of the present disclosure but to describe the technical idea of the present disclosure, and the technical spirit of the present disclosure is not limited by these embodiments.

The scope of protection of the present disclosure should be interpreted by the appending claims, and all technical ideas within the scope of equivalents should be construed as falling within the scope of the present disclosure.

What is claimed is:

1. An X-ray imaging apparatus comprising:
   an X-ray generator comprising a plurality of X-ray sources disposed in a form of a two-dimensional array;
   an X-ray detector configured to detect X-rays radiated from the plurality of X-ray sources and generate a plurality of pieces of projection data; and
   a processor configured to:
   apply log projection to each of the plurality of pieces of projection data;
   apply weighted projection to the log-projected projection data;
   apply a bidirectional ramp filter to the weighted-projected projection data; and
   generate a reconstructed tomographic image based on each of the plurality of pieces of projection data to which the bidirectional ramp filter is applied,
   wherein the plurality of pieces of projection data includes:
   a first projection data generated based on the processor controlling the plurality of X-ray sources to be turned on sequentially along a first dimension of the array, to radiate X-rays to an object to be captured in a first direction corresponding to the first dimension; and
   a second projection data generated based on the processor controlling the plurality of X-ray sources to be turned on sequentially along a second dimension of the array, to radiate X-rays to the object to be captured in a second direction corresponding to the second dimension, and
   wherein the processor is further configured to obtain the first projection data by applying the bidirectional ramp filter to the weighted-projected projection data in the first direction, and the second projection data by applying the bidirectional ramp filter to the weighted-projected projection data in the second direction.

2. The X-ray imaging apparatus of claim 1, wherein the processor is further configured to generate a normalized reconstructed tomographic image by applying normalization to the reconstructed tomographic image.

3. The X-ray imaging apparatus of claim 2, wherein the processor is further configured to repeat an iterative reconstruction process with respect to the normalized reconstructed tomographic image until an iteration criterion is satisfied.

4. The X-ray imaging apparatus of claim 3, wherein the processor is further configured to perform the iterative reconstruction process by:
   obtaining the normalized reconstructed tomographic image as a first tomographic image;
   obtaining a plurality of pieces of virtual projection data by performing forward projection on the first tomographic image based on coordinates of each of the plurality of X-ray sources;
   obtaining a difference by comparing the plurality of pieces of projection data with the plurality of pieces of virtual projection data based on the coordinates of each of the plurality of X-ray sources;
   performing back-projection by applying weighted projection to the obtained difference to obtain a back-projected image difference; and
   obtaining a second tomographic image by applying normalization based on the back-projected image difference and the first tomographic image.

5. The X-ray imaging apparatus of claim 4, wherein the processor is further configured to:
   determine whether a particular number of iterations is satisfied; and
   repeat the iterative reconstruction process by iteratively using the second tomographic image as the first tomographic image based on the particular number of iterations not being satisfied.

6. An X-ray image processing method for performance by an X-ray imaging apparatus, the method comprising:
   obtaining a plurality of pieces of projection data;
   applying log projection to each of the plurality of pieces of projection data;
   applying weighted projection to the log-projected projection data;
   applying a bidirectional ramp filter to the weighted-projected projection data; and
   generating a reconstructed tomographic image based on each of the plurality of pieces of projection data to which the bidirectional ramp filter is applied,
   wherein the X-ray imaging apparatus comprises an X-ray generator comprising a plurality of X-ray sources disposed in a form of a two-dimensional array,
   wherein the plurality of pieces of projection data includes:

a first projection data generated based on controlling the plurality of X-ray sources to be turned on sequentially along a first dimension of the array, to radiate X-rays to an object to be captured in a first direction corresponding to the first dimension; and a second projection data generated based on controlling the plurality of X-ray sources to be turned on sequentially along a second dimension of the array, to radiate X-rays to the object to be captured in a second direction corresponding to the second dimension, and wherein the first projection data is obtained by applying the bidirectional ramp filter to the weighted-projected projection data in the first direction, and the second projection data is obtained by applying the bidirectional ramp filter to the weighted-projected projection data in the second direction.

7. The X-ray image processing method of claim 6, further comprising generating a normalized reconstructed tomographic image by applying normalization to the reconstructed tomographic image.

8. The X-ray image processing method of claim 7, further comprising repeating an iterative reconstruction process with respect to the normalized reconstructed tomographic image until an iteration criterion is satisfied.

9. The X-ray image processing method of claim 8, wherein the iterative reconstruction process comprises:

obtaining the normalized reconstructed tomographic image as a first tomographic image;

obtaining a plurality of pieces of virtual projection data by performing forward projection on the first tomographic image based on coordinates of each of the plurality of X-ray sources;

obtaining a difference by comparing the plurality of pieces of projection data with the plurality of pieces of virtual projection data based on the coordinates of each of the plurality of X-ray sources;

performing back-projection by applying weighted projection to the obtained difference to obtain a back-projected image difference; and obtaining a second tomographic image by applying normalization based on the back-projected image difference and the first tomographic image.

10. The X-ray image processing method of claim 9, further comprising:

determining whether a particular number of iterations is satisfied; and repeating the iterative reconstruction process by iteratively using the second tomographic image as the first tomographic image based on the particular number of iterations not being satisfied.

* * * * *